United States Patent [19]

Szybalski

[11] Patent Number: 4,774,182

[45] Date of Patent: Sep. 27, 1988

[54] PARTIALLY DEFECTIVE FOREIGN GENE FOR CONFERRING IMMUNITY ON A BIOLOGICAL HOST

[75] Inventor: Waclaw T. Szybalski, Madison, Wis.

[73] Assignee: Wisconsin Alumni Research Foundation, Madison, Wis.

[21] Appl. No.: 935,122

[22] Filed: Nov. 26, 1986

Related U.S. Application Data

[63] Continuation of Ser. No. 626,557, Jun. 29, 1984, abandoned.

[51] Int. Cl.[4] ...................... C12P 21/00; C12N 15/00; C12N 7/04; C12N 1/20

[52] U.S. Cl. .................................. 435/68; 435/172.1; 435/172.3; 435/236; 435/253; 935/11; 935/29; 935/72; 935/73; 935/74

[58] Field of Search ...................... 435/68, 172.3, 236, 435/240, 253

[56] References Cited

U.S. PATENT DOCUMENTS

| | | | |
|---|---|---|---|
| 4,332,897 | 6/1982 | Nakano et al. | 435/172 |
| 4,436,815 | 3/1984 | Hershberger et al. | 435/172 |
| 4,499,188 | 2/1985 | Konrad et al. | 435/68 |
| 4,530,904 | 7/1985 | Hershberger et al. | 435/68 |

OTHER PUBLICATIONS de la Peña et al. *Nature* 325: 274–276, 1987.
Schumann, W. *Gene* 5:275–290, 1979.
Devash et al. *Virology* 111:103–112, 1981.
Vlazny et al., *Proc. Natl. Acad. Sci.* (USA) 78:742–746, 1981.
Herrera–Estrella et al. *Nature* 303:209–213, 1983.
Smith et al. *Wisconsin State Journal,* Apr. 17, 1986.
Abel et al. *Science* 232:738–743, 1986.
Steinberg et al. *P.N.A.S.* 75(11):5594–5598, 1978 (Nov.).
Cassells et al. *Virology* 78:253–260, 1977.
Potrykus et al. *MGG* 199:183–188, 1985.
Froman et al. *Nature* 319:791–793, 1986.
Lörg et al. *MGG* 199:178–182, 1985.
Bernard, H. et al. 1979, Gene 5:59–76.
Page 9 of the Mar./Apr., 1982 *Genetic Engineering News,* an article entitled "Anti-Genes Wreak Havoc".
W. F. Stevens, S. Adhya, W. Szybalski, "Origin and Bidirectional Orientation of DNA Replication In Coliphage Lambda", in *The Bacteriophage Lambda,* A. D. Hershey Ed. pp. 515–533 (1971) (Cold Springs Harbor, N.Y.).
E. H. Szybalski and W. Szybalski, *A Comprehensive Map of Bacterio-Lambda,* 7 Gene 217–270 (1979).
E. H. Szybalski and W. Szybalski, *Physical Mapping of the att–N Region of Coliphage Lambda,* etc. 56 Biochimie 1497–1503 (1974).
H.-J. Rehm & G. Reed, *Biotechnology,* vol. 1, Chapter 5b "Mutations" (1983).
J. Setlow and A. Hollaender (Eds.), *Genetic Engineering: Principles and Methods,* vol. 1, "Constructed Mutants of Simian Virus 40", pp. 73 et seq. (1983).
J. S. Salstrom and W. Szybalski, *Coliphage Lambda nutL: A Unique Class of Mutants Defective In The Site of Gene N Product Utilization For Antitermination of Left-hand Transcription,* 124 J. Mol. Biol. 195–221 (1978).
T. S. Papas, et al., *Gene Amplification And Analysis,* vol. 3, Chapter 8 "High Level Expression of Oncogenes in *E. coli*" (1983).
T. Kosuge et al., *Genetic Engineering of Plants,* pp. 143 et seq. (1983).
Y. Gluzman, *Eukaryotic Viral Vectors,* Cold Spring Harbor (1982).

*Primary Examiner*—Thomas G. Wiseman
*Assistant Examiner*—Thomas D. Mays
*Attorney, Agent, or Firm*—Quarles & Brady

[57] ABSTRACT

Construction of a recombinant bacterial host which is substantially immune to a normally infectious viral agent is disclosed. In one embodiment a foreign recombinant reproducible gene segment is inserted into the bacterial cell. The gene segment is a partially defective variant of a gene segment from the infectious virus of interest. The viral gene segment, in its naturally occurring and fully operational form, normally codes for a non-repressor protein which participates in a multi-protein complex used in the development of the virus. However, the partially defective gene present in the bacterial cell codes for a defective protein that will bind to the remainder of the multi-protein complex with a greater affinity than the virus' fully operational protein. The "new" protein complex will therefore be inactive and will inhibit the ability of the foreign agent to use the multi-protein complex for its development.

3 Claims, 2 Drawing Sheets

GENE O
GENE X
GENE P
GENE P* (MUTANT)
P PROTEIN
O PROTEIN
P* PROTEIN
X PROTEIN

PARTIALLY DEFECTIVE FOREIGN GENE FOR CONFERRING IMMUNITY ON A BIOLOGICAL HOST

This application is a continuation of application Ser. No. 626,557, filed June 29, 1984, now abandoned.

FIELD OF THE INVENTION

The invention relates to a way of conferring immunity upon unicellular or multicellular organisms (biological hosts) to an infectious foreign biological agent. More particularly, it relates to a way of modifying a host cell using recombinant DNA techniques so that the host cell will produce a special proteinaceous material that interferes with the development of the infectious agent.

DESCRIPTION OF THE ART

One of the great concerns of plant and animal producers is the possibility that their investment can be partially or totally destroyed by an infectious disease. Depending on the particular disease, various techniques have been tried to attempt to solve the problem. In some cases, vaccines that stimulate natural antibody production have been developed. In other cases, drugs have been developed to slow the progress of the disease and/or to alleviate the symptoms. In still other cases, there have been attempts to produce disease-resistant plants or animals by selection of naturally resistant varieties, and by appropriate breeding selection.

One or more of these techniques have proved successful for some diseases and hosts. However, many diseases appear still not easy to prevent. Also, even where one or more of these techniques will work, the costs can sometimes be quite high.

Another consideration is that some of the best of these prior art approaches are unsuitable for certain types of hosts. For example, because plants do not develop antibodies, a vaccine-type approach will normally not be successful in a plant system.

Another related problem occurs when microorganisms are the host of interest, and the microorganisms are being used in a recombinant DNA commercial process to produce a protein of interest. It is desirable in such systems to maximize yields by rendering the microorganisms immune to infection (usually by various viruses). However, for some such "diseases" microorganisms do not have natural immunity. Thus, it can be seen that a need exists for an improved way to confer immunity to a wide variety of infectious agents on a wide variety of biological hosts.

SUMMARY OF THE INVENTION

In one aspect of the invention, there is provided a recombinant biological host which is substantially immune to a normally infectious foreign agent. To achieve this immunity, the host has been provided with a foreign recombinant gene which is a partially defective variant of a gene segment from the foreign agent. The gene segment from the foreign agent, in its naturally occurring and fully operational form, normally expresses a proteinaceous material which often participates in a multi-protein complex used in the development of the foreign agent. However, the variant gene codes for a modified proteinaceous material that will still bind to the remainder of the multi-protein complex, but is otherwise defective, and thus will inhibit the ability of the foreign infectious agent to use the multi-protein complex for development.

In an especially preferred form, the defective proteinaceous material actually has a greater affinity for the multi-protein complex than the normally expressed proteinaceous material does. This allows the defective proteinaceous material to out-compete the "good" proteinaceous material produced by the infecting agent.

Because plants (in contrast to higher animals) lack the antibody-producing system, and because there are fewer ethical or emotional aspects involved with genetically engineering plants than animals, the preferred hosts are plants. However, it is believed that the invention will confer immunities on a wide variety of animals, microorganisms, and other biological hosts. Also, while the infectious agent of initial interest is a bacterial virus, there appears to be no reason why many other types of infectious agents (e.g., bacteria, products of ocogenes) cannot be immunized against, using the basic principles of the invention.

As an especially desirable feature, the foreign variant ("dominant-lethal") gene can be controlled by a second foreign sequence (e.g., a transcriptional terminator), such that the second foreign sequence normally inhibits expression of the defective proteinaceous material when the host is not infected by the foreign agent, yet permits the expression of the defective proteinaceous material when the host is infected by the foreign agent (e.g., one that carries an anti-termination system). This minimizes waste, and minimizes the likelihood of side effects.

Another appropriate recombinant gene can be introduced into the cell so as to allow a temperature change to trigger production of the defective material (so for example only a sick animal that is running an elevated temperature will have the defective material produced).

In yet another aspect of the invention, the development of the infectious agent can be inhibited by exposing infected cell to a safe and effective amount of the defective proteinaceous material.

In practicing the principles of the present invention, one will normally first select an appropriate gene that is present in the infectious agent, and a connected control sequence. The gene will be selected because it produces a proteinaceous material that is part of a multi-protein complex needed for development of the infectious agent. For virus systems, this could be a gene coding for a viral protein participating in its replication or expression complex, or a protein involved in viral coat formation, or other multi-protein complex proteins. For other infectious agent systems, analogous components of a multi-protein complex will normally be chosen. The gene should also be selected so that the defective proteinaceous material produced from a variant of the gene is not toxic to the host.

Once the gene has been selected, it is then separated from most of the remainder of the genetic material of the foreign agent (usually a promoter and/or terminator sequence is kept intact with the gene), and inserted by recombinant DNA or analogous techniques into the first host cell such as a bacteria (e.g., by inserting it into the host chromosome, or by carrying it into the cell on a suitable cloning vehicle such as a plasmid). The next step is mutagenesis of the cloned gene. One can rely upon natural mutations, or one can induce mutations by one of the various known techniques.

An important facet of the present invention is the realization that the mutants can then be easily selected by exposing the reaction mixture or the culture to the infectious agent. Only those few cells that have developed a survival mechanism will survive.

One then looks for those cells where the mutated proteinaceous material still interacts with the active complex, and the complex in turn loses its function. Preference is given to cells where the defective material has an increased affinity for the protein complex relative to the natural proteinaceous material.

Thus, by using the principles of the present invention, the "dominant-lethal" proteinaceous material will tie up several of the vital components of development of the infectious agent (the other portions of the protein complex). This is somewhat analogous to mounting a broken or otherwise defective gear into a gear box and letting the engine try to run.

After one has isolated the appropriate clone, one can then grow it up to a large culture. Thereafter, one can use the culture as a source of the defective gene and transfer the gene using other vectors to other hosts (e.g., plants or animals) in order to protect them from the specific infectious agent.

As another added feature, one can in some cases choose the defective proteinaceous material so that it also serves as an enriched food source for those who eat the protected host for food. Thus, not only will the defective material establish a new kind of immunity, but it will also provide an extra food source for anyone eating the host.

The objects of the invention therefore include:

(a) providing a recombinant biological host of the above kind which is substantially immune to a normally infectious foreign agent;

(b) providing a recombinant biological host of the above kind which produces a defective proteinaceous material that interferes with the development of an infectious foreign agent;

(c) providing a recombinant biological host of the above kind which produces the defective proteinaceous material only when the host is attacked by the infectious agent; and (d) providing a method of inhibiting development of an infectious agent in which the defective proteinaceous material produced by the recombinant biological host is appropriately delivered so as to inhibit development of the infectious agent, and thereby controls the disease.

These and still other objects and advantages of the present invention will be apparent from the description that follows. In the following description, the preferred embodiments of the invention will be disclosed. These embodiments do not represent the full scope of the invention. Rather, the invention may be employed in still other embodiments. Reference is therefore to be made to the claims herein for interpreting the full scope of the present invention.

DESCRIPTION OF THE PREFERRED EMBODIMENTS

EXAMPLE 1

Immunity has been conferred upon a host bacterium *E. coli* to bacterial virus lambda infection by isolation of "dominant-lethal" mutants of cloned lamda genes O and/or P. The laboratory procedures used will be described below.

The starting material was *E. coli* SA431. This bacterial host already contains the lambda virus in the prophage form, but the genes (O)-S-R-A-J-attR on the "right-hand side" of the prophage genome have already been deleted (see FIG. 2). Also, this virus has already been provided on the "left-hand side" with a thermosensitive mutation cIts857, which controls production of the O and P gene products from the pR promoter. The *E. coli* SA431 strain is described in detail in W. F. Stevens, S. Adhya and W. Szybalski, "Origin And Bidirectional Orientation Of DNA Replication In Coliphage Lambda" in *The Bacteriophage Lambda* (Hershey, A.D., Ed.), Cold Spring Harbor Laboratory, Cold Spring Harbor, N.Y., pp. 515–533 (1971). (This article and all other articles referred to herein are incorporated by reference as if fully set forth below). *E. coli* SA431 is also available from the collection of the Laboratory Of Molecular Biology, National Cancer Institute, N.I.H., Bethesda, Md., 20205.

In the first step, I deleted lambda prophage "left hand" genes attL-red-ral from SA431, and replaced them with host bio genes by lysogenizing strain SA431 with phage lambda bio10. Phage lambda bio10 (see FIG. 2) can be obtained from the collection of Laboratory Of Molecular Biology, National Cancer Institute, N.I.H., Bethesda, Md., 20205. The laboratory procedures used for lysogenizing the strain SA431 with lambda bio10 are as follows:

Strain SA431 is doubly lysogenized (see the intermediate of FIG. 2) by infection with lambda bio10 phage in a minimal starvation medium at 32° C. Double lysogens are identified as bright-red bio+ colonies on the tetrazolium medium (overnight, 32° C). Cultures of such double lysogens SA431 (lamba bio10), when grown at 30° C. and then induced for 30 minutes at 42°, and subsequently grown at 30° C., will lyse and produce lambda cIts857 phage recombinants. See also E. H. Szybalski and W. Szybalski, *A Comprehensive Map Of Bacteriophage Lambda,* 7 Gene 217–270 (1979) (FIGS. 2 DE&E of this paper show that the bio substitution covers the lambda region between attR and N.-); and E. H. Szybalski and W. Szybalski, *Physical Mapping Of The att-N Region Of Coliphage Lambda, etc.* 56 Biochimie 1497–1503 (1974) (physical structure and derivation of bio10).

Figure 1:
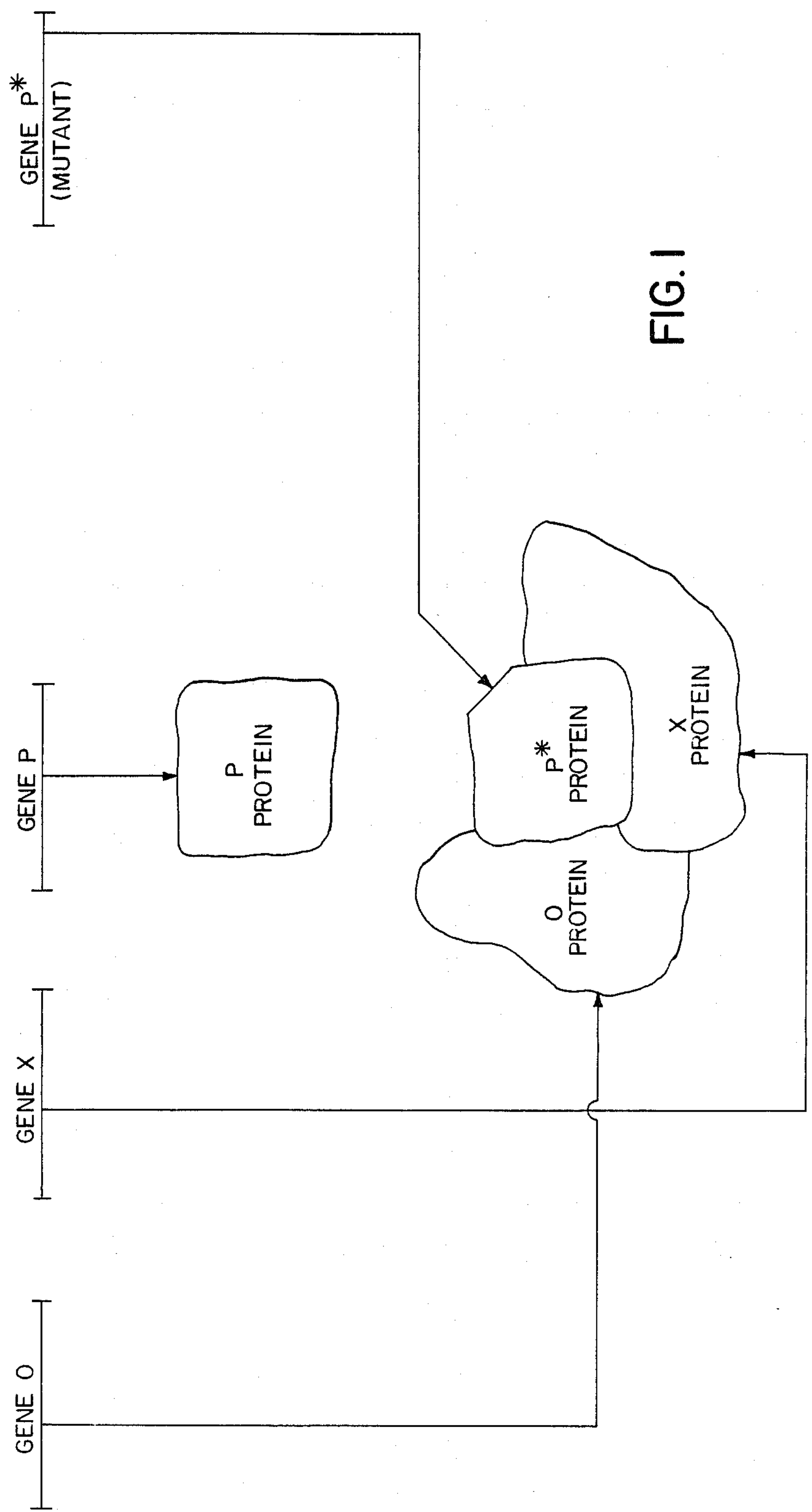
FIG. 1 is a schematic depiction of how a multiprotein complex can bind to a defective protein p* in preference to the normal protein P.
Figure 2:
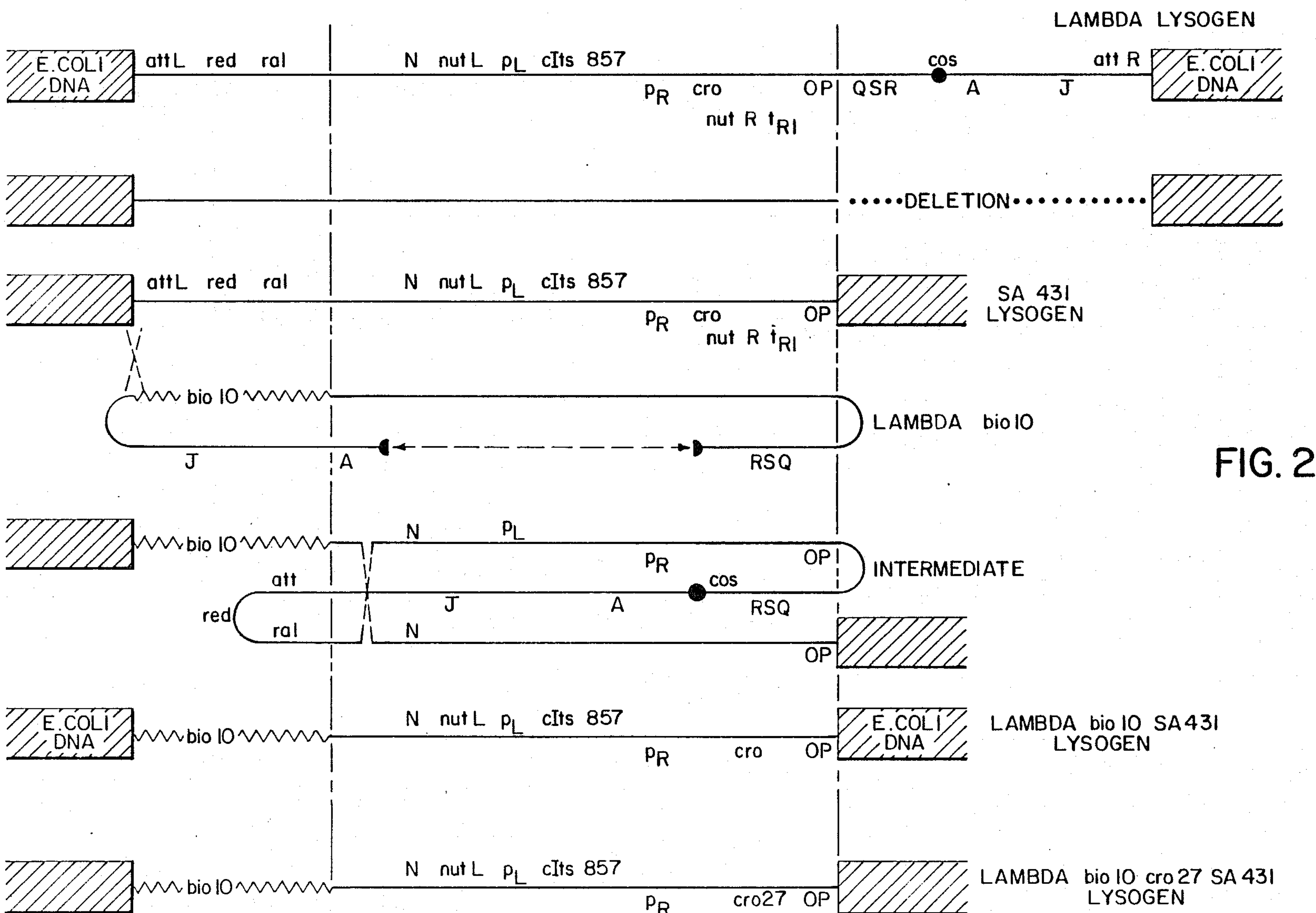
FIG. 2 is a schematic view of the alteration of the phage lambda gene sequence as described in Example 1.

I then prepared and selected lysogens that had lost the complete lambda prophage (lambda bio 10 SA 431 in FIG. 2). To do this, the doubly lysogenic intermediate was grown at 30° C. and then grown for 5 minutes at 42° C. (to induce prophage), followed by plating colonies at 30° C. Fifty cultures were started from separate colonies, and those selected were those which did not produce viable phage upon further 42° C. induction. They had lost a complete prophage, leaving behind lambda bio 10 SA 431 which carries only the lambda gene sequence of interest, N-nutL-pL-cIts 857-pR-cro-nutR-tRl-O-P-The N gene-product counters termination, nutL is a recognition site for the N product, pL promotes the -N expression, Its857 represses expression only below certain temperatures and allows expression above it, pR promotes expression of the cro, O and P genes, cro is a repressor, nutR is a recognition site for the N product, tRl is a terminator, and and P are the genes of interest. For other genes of interest from this or other infectious agents, one can devise appropriate similar schemes to isolate the relevant gene of interest and to subject them to the control of appropriate promoters and/or terminators.

The resulting fragment of the lambda virus is repressed by the Its857 product at 30° C., but is induced at 42° C. because of the thermosensitivity of its cIts857 repressor protein. Thus, heating of the *E. coli* strain containing lambda bio10 SA431 to 42° C. for extended periods results in the expression of the pL-N operon and the pR-cro-t-Rl-O-P- operon, with resultant cell death due to the lethal effects of the O and P products. To insure even greater production of O and P at elevated temperatures, one can construct a cro-defective variant (cro 27). To do this, one takes lambda cro27SA431, which is available from the Laboratory Of Molecular Biology, National Cancer Institute, N.I.H., Bethesda, Md. 20205, and using procedures similar to those above causes replacement of cro+by the cro27 mutation. The cro gene-coded repressor is thus rendered inactive by replacing it with a "defective" cro27 gene.

It should be appreciated that the approach above began with a part of the lambda genome and a heat-sensitive controller already in the host. However, for other infectious foreign agents vectors such as plasmids can be used to carry an appropriately modified gene sequence into the appropriate initial host cell.

After one has the desired gene sequence in the *E. coli* host, one can either rely on spontaneous mutations occurring, or one can induce mutation by one of the known techniques. See e.g., H.-J. Rehm and G. Reed, *Biotechnology,* Volume 1, Chapter 5b "Mutations" (1983); J. Setlow and A. Hollaender (Eds.), *Genetic Engineering: Principles And Methods,* Volume 1, "Constructed Mutants Of Simian Virus 40" pp. 73 et seq (1983).

Then, by selecting for host mutants that (1) survive at 42°, when the lambda lysogen is induced, and (2) survive lambda infection at 42° C. but do not survive at 32° C., one can isolate one or more mutants that make defective (dominant lethal) O and/or P proteins. It should be noted that the realization of how one can spot the mutants is an important aspect of the invention, for if one did not realize that by challenging the cells with the infectious agent one could spot likely candidates, and that one could confirm this by turning off the immunity and then rechallenging, one would not know how to find the right cell.

Using this principle, I isolated over thirty of 42° C. survivors, which were tested by appropriate genetic crosses for the presence of mutations in genes O and P. To confirm the existence of the $O^-$ or $P^-$ mutation, I superinfected the induced lambda bio10 $O/P^{-d}$ SA431 lysogen (−d superscript indicates dominant lethal mutation in gene O or P) with phage phi 80. This phage has a gene O different and gene P very similar to that of lambda. Plaque formation of phi 80 on the induced lysogen indicated mutation in O and absence of phi 80 indicated dominant-lethal mutation in gene P.

It will be appreciated that in some animals, when an infecting agent takes hold, the animal will develop an elevated temperature. Thus, use of a temperature trigger gene like cIts857 can provide a means of activating the cells defenses just when the animal has become infected. Obviously, for certain animals analogous genetic temperature triggers which respond more closely to slight increases in natural body temperature may have to be developed, but these triggers will be variants of the basic principle disclosed herein.

A culture of *E. coli* lysogen lambda bio10 $O/P^{-d}$ SA431 is deposited with ATCC No. 39625, and samples are available from the permanent collection of the American Type Culture Collection of Rockville, Md. 20852. This deposit and all other ATCC deposits hereunder are available to the public upon the grant of a patent to the assignee disclosing them. They are also available as required by foreign patent laws in countries wherein counterparts of the subject application or its progeny may be filed. However, it should be understood that the availability of a deposit does not constitute a license to practice the subject invention in derogation of patent rights granted by governmental action.

EXAMPLE 2

A second bacterial construct was created that permits expression of the dominant-lethal gene only in the presence of the lambda viral protein. In the construct described in Example 1, the defective O and P genes expressed protein continuously above 39° C. Since continuous expression may be of disadvantage to the host cell (e.g., by using up otherwise needed materials, and/or by producing harmful side effects), and since for some animals it may not be possible to find a temperature trigger that is sensitive enough to act at the exact point when an infection takes hold, it is desirable to provide a model system in which the activity of the infectious agent will itself turn the system on.

Using procedures described in more detail below, we inactivated the cI-coded repressor of the above described virus, and also inserted an additional terminator IS2 - between the tRl site and the O gene. See generally J. S. Salstrom and W. Szybalski, *Coliphage Lambda nutL: A Unique Class Of Mutants Defective In The Site Of Gene N Product Utilization For Antitermination Of Lefthand Transcription,* 124 J. Mol. Biol. 195–221 (1978). The IS2 element (carrying the IS2 terminator) and the corresponding $N^-$ mutations are obtained from phage lambda N7N53c857r32 (mutation r32 is the IS2 insertion), which is deposited with ATCC as number 40120. The $cI^-$ mutation is obtained from phage lambda IKH100 (KH100 is the IS5 insertion into gene cI) which is deposited with ATCC as number 40119. The procedure for crossing-in the $N^-$, $cI^-$ and r32 mutations is analogous to that described by Salstrom and Szybalski above.

The IS2 terminator was selected because it is responsive to N anti-termination. In the absence of N product, the tRl and IS2 terminators will operate. However, when N protein is provided, it will prevent tRl and IS2 from terminating. Thus, given that the cI repressor gene has been made inactive by the cIKH100 mutation, the O and P genes will be produced at any temperature, *but only when the N product is supplied.*

Therefore, upon infection with lambda virus, the N product *of the invading virus* anti-terminates the tRl and IS2 blocks in the transcription, and the resulting synthesis of the mutant O or P products blocks the further development of the invading virus.

EXAMPLE 3

Conferring viral immunity upon the host bacterium can also be accomplished by isolation of cloned lambda genes coding for lambda head and tail components. The two examples above have involved the genes O and P that are involved in the reproduction of the virus. The invention has also worked with a wide variety of other lambda variant genes that are dominant-lethal mutants of the head and tail genes A–J of the virus.

EXAMPLE 4

While the examples above have dealt solely with a model system, bacteria being made immune to viruses, it will be apparent to those skilled in the art that similar techniques can be used for other hosts and genes of other infectious agents, even oncogenes. See, e.g., T. S. Papas et al. *Gene Amplification And Analysis,* Volume 3, Chapter 8 "High Level Expression Of Oncogenes In *E. coli*" (1983).

Once the proper gene has been isolated and introduced into a primary test host, such as a bacterium, this gene can then be mutated to the "dominant-lethal" kind, inserted into a new desirable vector, and then transferred into a plant and/or animal, using what have now become conventional recombinant techniques. An example of a vector for carrying a gene into a plant is that described in T. Kosuge et al. *Genetic Engineering Of Plants,* pp. 143 et seq (1983). An example of a vector for carrying a gene into an animal cell is described in Y. Gluzman, *Eukaryotic Viral Vectors,* Cold Spring Harbor (1982).

While one can insert into animals (such as humans) these anti-infection factories to prevent illness, some individuals believe that there might be ethical problems involved in "human" engineering, and there could possibly be adverse side reaction problems to be overcome in some cases. Thus, while this application of the invention should theoretically work well for humans in many cases, a simpler approach is to use the defective gene product itself to directly treat an infected mammalian cell. Thus, after studies on the protein uptake problem and suitable testing, one can simply expose the infected cell to the proteinaceous material as a means of suppressing the infection.

Of course, as stated above, providing plants with immunity to virus infection appears to be a major advantage of the present invention. This is especially useful since plants have no naturally occurring immune system of their own.

It will be appreciated that the present invention therefore provides a means for immunizing a wide variety of host cells to a wide variety of infectious agents, and/or treating a cell once infected. Although the especially preferred embodiments of the present invention have been described above, it should be noted the invention is not to be so limited. In this regard, there may be various other modifications and changes to these embodiments which are well within the scope of the invention. For example, the defective proteinacous material of choice can be selected so that at the same time the protein confers immunity upon a plant, it also provides an additional nutrient needed by humans. Also, since the infectious agent could slowly develop resistance to the approach described, one might combine more than one dominant-lethal gene to increase the effectiveness of the technique. This modification and other modifications are meant to be within the scope of the invention.

I claim:

1. A bacteria cell which inhibits through man-made means the development of a virus normally infections to said cell, comprising:

a foreign recombinant gene segment in the bacteria cell having a defective variant of a gene segment from the normally infectious virus;

said variant having been created by a mutation of said normal gene segment, said mutation having been induced by man;

said gene segment from the normal infectious virus, in its naturally occurring fully operation form, normally expressing a proteinaceous material that is not a repressor protein and which participates in a protein complex of at least two molecules, said complex being used in the structure, replication, or expression of the virus; and said defective variant producing a defective proteinaceous material that will bind with at least part of the remainder of said complex and will inhibit the ability of the virus to develop, said inhibition being caused by the binding of the defective proteinaceous material to said remainder of the complex.

2. A method of inhibiting development of a virus normally infectious to a bacteria cell through man-made means, comprising:

selecting a virus which is of a type having a gene segment that expresses a proteinaceous material that is not a repressor protein and which participates in a protein complex of at least two molecules, said complex being used in the structure, replication, or expression of the virus;

obtaining a defective variant of said proteinaceous material that will bind with at least part of the remainder of the complex;

said defective proteinaceous variant having been expressed by a mutation of said gene segment, said mutation having been induced by man; and subjecting a bacteria cell to the defective variant of said proteinaceous material in sufficient quantity so as to cause inhibition of development of the virus in the cell, said inhibition being caused by the binding of the defective proteinaceous material to said remainder of the complex.

3. A bacteria cell which inhibits through man-made means the development of a virus normally infectiou to said cell, comprising:

a foreign recombinant gene segment in the bacteria cell having a defective variant of a gene segment from the normally infectious virus;

said variant having been created by a mutation of said normal gene segment, said mutation having been induced by man;

said gene segment from the normal infectious virus, in its naturally occurring fully operational form, normally expressing a proteinaceous material that is not a repressor protein and which participates in a protein complex of at least two molecules, and complex being used in the structure, replication, or expression of the virus;

said defective variant producing a defective proteinaceous material that will bind with at least part of the remainder of said complex and will inhibit the ability of the virus to develop, said inhibition being caused by the binding of the defective proteinaceous material to said remainder of the complex; and the defective gene sequence is controlled by a second gene sequence such that the second sequence normally inhibits the expression of the defective gene when the bacteria cell is not infected by the virus and triggers expression of the defective gene when the bacteria cell is infected by the virus.

* * * * *

UNITED STATES PATENT AND TRADEMARK OFFICE

CERTIFICATE OF CORRECTION

PATENT NO. : 4,774,182

DATED : September 27, 1988

INVENTOR(S) : Waclaw T. Szybalski

It is certified that error appears in the above-identified patent and that said Letters Patent is hereby corrected as shown below:

Immediately after the title in column 1, the following paragraph was omitted:

The invention was made with United States government support awarded by the National Institutes Of Health (NIH) Grant #CA23076. The United States Government has certain rights in this invention.

Column 3, line 58 "p*" should read --P*--

Column 5, line 5 "Its857" should read --cIts857--

Column 5, line 8 "SA431" should read --SA431 prophage--

Column 6, line 40 "N7N53c857r32" should read --N7N53cI857r32--

Column 6, line 42 "IKH100" should read --cIKH100--

Column 8, line 8 "operation" should read --operational--

Column 8, line 41 "infectiou" should read --infectious--

UNITED STATES PATENT AND TRADEMARK OFFICE

CERTIFICATE OF CORRECTION

PATENT NO. : 4,774,182

DATED : September 27, 1988

INVENTOR(S) : Waclaw T. Szybalski

It is certified that error appears in the above-identified patent and that said Letters Patent is hereby corrected as shown below:

Column 8, line 53, "molecules, and" should read --mole cules, said--

Signed and Sealed this

Twenty-eighth Day of February, 1989

Attest:

DONALD J. QUIGG

*Attesting Officer*

*Commissioner of Patents and Trademarks*

CERTIFICATE OF CORRECTION

PATENT NO. : 4,774,182

DATED : September 27, 1988

INVENTOR(S) : Waclaw T. Szybalski

It is certified that error appears in the above-identified patent and that said Letters Patent is hereby corrected as shown below:

Immediately after the title in column 1, the following paragraph was omitted:

The invention was made with United States government support awarded by the National Institutes Of Health (NIH) Grant #CA23076. The United States Government has certain rights in this invention.

Column 3, line 58 "p*" should read --P*--

Column 5, line 5 "Its857" should read --cIts857--

Column 5, line 8 "SA431" should read --SA431 prophage--

Column 6, line 40 "N7N53c857r32" should read --N7N53cI857r32--

Column 6, line 42 "IKH100" should read --cIKH100--

Column 8, line 8 "operation" should read --operational--

Column 8, line 41 "infectiou" should read --infectious--

UNITED STATES PATENT AND TRADEMARK OFFICE

CERTIFICATE OF CORRECTION

PATENT NO. : 4,774,182

DATED : September 27, 1988

INVENTOR(S) : Waclaw T. Szybalski

It is certified that error appears in the above-identified patent and that said Letters Patent is hereby corrected as shown below:

Column 8, line 53 "mole cules, and" should read --molecules, said--

This certificate supersedes Certificate of Correction issued February 28, 1989.

Signed and Sealed this

Twenty-fifth Day of July, 1989

Attest:

DONALD J. QUIGG

Attesting Officer

Commissioner of Patents and Trademarks